United States Patent [19]

Ward

[11] Patent Number: 5,050,470
[45] Date of Patent: Sep. 24, 1991

[54] RECEIVER FOR SPECIMENS FROM CRYOGENIC MICROTOME

[76] Inventor: John L. Ward, 1006 Barnwell St., Columbia, S.C. 29601

[21] Appl. No.: 352,044

[22] Filed: May 15, 1989

[51] Int. Cl.⁵ .............................................. G01N 1/06
[52] U.S. Cl. ........................................ 83/167; 83/166; 83/915.5
[58] Field of Search ................ 83/167, 94, 915.5, 166, 83/111; 53/513, 520, 435, 266 C

[56] References Cited

U.S. PATENT DOCUMENTS

| | | | |
|---|---|---|---|
| 3,680,420 | 8/1972 | Blum | 83/167 |
| 3,699,830 | 10/1972 | Pickett | 83/915.5 |
| 3,723,226 | 3/1973 | Pfohler | 83/915.5 |
| 3,832,923 | 9/1974 | Lassmann et al. | 83/16 |
| 3,924,500 | 12/1975 | Kindel | 83/167 |
| 3,978,686 | 9/1976 | Lechner et al. | 62/514 R |
| 4,024,779 | 5/1977 | Taugner et al. | 83/165 |
| 4,472,989 | 9/1984 | Endo | 83/162 |

FOREIGN PATENT DOCUMENTS

2506255 9/1976 Fed. Rep. of Germany ..... 83/915.5

Primary Examiner—Hien H. Phan
Attorney, Agent, or Firm—Dority & Manning

[57] ABSTRACT

A receiver for specimen slices, produced by slicing a tissue sample in a cryogenic microtome, includes an upper member pivotably attached to a lower member and forming a space therebetween for receipt of the specimen slices. Such receipt prevents curling and rolling of the slices, and facilitates easy transfer of the slices to an examination slide. The receiver is adapted to be pivotably and adjustably attached to the microtome, whereby it can be selectively pivoted away from the specimen slice receiving position, or otherwise adjusted for optimized tissue slice reception and storage.

28 Claims, 5 Drawing Sheets

RECEIVER FOR SPECIMENS FROM CRYOGENIC MICROTOME

BACKGROUND OF THE INVENTION

The present invention generally relates to improvements in handling specimen slices cut by a microtome, and particularly relates to preventing curling of tissue slices cut by a cryogenic microtome.

For the purpose of making microscopic examinations of tissue samples, a tissue sample is typically placed in a microtome so that it can be sliced into thin specimens for staining and examination. Use of a cryogenic microtome and frozen tissue samples facilitates rapid examination in situations where an immediate diagnosis is necessary. Whether cryogenic or room temperature conditions prevail, it is imperative for proper diagnosis that a good cross-section of the sample be sliced and that the resultant slice be properly stored, that is prevented from curling or twisting or the like.

Heretofore, it has been known to provide a shield attached to the microtome. For example, in one known instance the shield is located proximate to the blade such that as the sample is sliced, the specimen slice is forced below the shield and along the top of the blade. It is then necessary to relocate the shield for access to the blade, and then transfer the specimen slices from the blade onto a slide for staining and diagnosis. The slices are lifted from the blade typically by placing a slide at room temperature quickly against the slices. The temperature differential causes the slices to adhere to the slide. It is extremely important that the specimen slices be prevented from rolling or curling or otherwise deforming in any manner which would prevent a flat, even cross-section from adhering to the slide for examination.

Although generally adequate for its intended purpose, such a known shield device forces the specimen slices to go along the microtome blade and away from the direction that they would naturally take due to the forces exerted by the blade during cutting. Furthermore, the presently known shield only directs the specimen slices toward the blade at the edge of the blade. Hence, as subsequent specimen slices engage the earlier slices (which have already adhered to or are resting on the blade) to force same to slide along the blade, the shield provides no mechanism for maintaining the specimen slices in a flat orientation so as to prevent them from curling, particularly when the shield is lifted.

Also, such a known shield requires frequent adjustment and considerable skill to obtain the necessary quality specimen slices. In addition, it is necessary to relocate the shield and remove the specimen slices from the microtome blade in some manner. In any event, static electricity may cause the slices to undesirably adhere to the shield rather than the blade, and thus may alter the slices causing them to be unusable. Because of these problems, many do not use this shield.

It has also been attempted to provide an anti-roll device to prevent curling of the slices. Such anti-roll device is a U-shaped member which extends down in front of the tissue sample and catches the specimen slice as it is cut, in a manner similar to a trapeze. Such a device requires considerable skill to operate and does not facilitate the transfer of the specimen slice onto a slide for microscopic examination. Further, it is difficult to keep the slices from falling off such device. Again, a typical result of such difficulties is that such device is not used in actual practice.

While various tissue slice handling problems can occur in virtually any type of microtome operations, the foregoing curling problems are particularly prevalent with frozen samples used during cryogenic operations. Room temperature tissue samples tend to have fewer curling problems since they are typically embedded with paraffin material.

SUMMARY OF THE INVENTION

The present invention recognizes and addresses the foregoing problems, and others, concerning microtome operations. Thus, broadly speaking, a principal object of this invention is improved microtome operations. More particularly, a main concern is improved receipt and/or handling of sample tissue slices produced from a microtome.

It is therefore another particular object of the present invention to provide an apparatus for preventing curling and/or rolling of specimen slices being produced with a microtome.

It is another general object of the present invention to provide an apparatus which facilitates successful transfer of non-deformed specimen slices for diagnosis.

Still a further more particular object is to provide an improved apparatus for receiving specimen slices from a cryogenic microtome.

Provision of an improved shield mechanism for receipt and storage of tissue slices is yet another present objective.

Additional objects and advantages of the invention are set forth, or will be apparent to those of ordinary skill in the art, from the detailed description which follows. Also, it should be appreciated that modifications and variations to the specific illustrated and discussed features hereof may be practiced in various embodiments and uses of this invention without departing from the spirit and scope thereof, by virtue of present reference thereto. Such variations may include, but are not limited to, substitution of equivalent means and features for those shown or discussed, and the reversal of various parts, or the like.

Still further, it is to be understood that different embodiments, as well as different presently preferred embodiments, of the present invention may include various combinations of presently disclosed features, or their equivalents. One exemplary such embodiment of the present invention relates to an improved shield mechanism for use with a microtome having a blade for cutting tissue slices from a tissue specimen. Such a present shield mechanism may comprise first and second members cooperatively arranged so as to define tissue slice receipt channel means therebetween and an opening to said channel; and may further comprise support means for supporting the first and second members relative the microtome such that the opening is situated relatively adjacent the microtome blade. With such a mechanism, tissue slices cut from a tissue specimen with the microtome enter the tissue slice receipt channel through the opening, for storage of such tissue slices within the receipt channel.

Another present exemplary embodiment concerns an apparatus adapted for receiving specimen slices from a cryogenic microtome of the type including cutting means for cutting a tissue sample to produce specimen slices. Such a present specimen slice receiving apparatus may include receptacle means for receiving specimen slices. The receptacle means preferably include a first end thereof for being located proximate the microtome cutting means, a second end located opposite such first end, an interior chamber for receiving specimen slices, and an opening defined proximate the first end and in communication with the interior chamber. The receptacle means of the present invention is adapted for receiving specimen slices into the interior chamber thereof, passing through the opening at the first end thereof.

Yet another construction comprising an exemplary embodiment includes an apparatus for use with a microtome, comprising generally planar receptacle means for receiving specimen slices, such receptacle means including a first end for being located proximate the microtome blade means and having an opening thereinto, a second end for being located distal of the microtome blade means, and a generally planar interior channel, whereby the receptacle means may receive specimen slices in a flat condition at the first end and store same within the interior channel thereof. Such receptacle means preferably includes an upper member pivotably attached to a lower member and adapted to be pivoted between respective opened and closed positions, such upper and lower members defining a substantially planar space therebetween comprising the interior channel when in the closed position so as to receive specimen slices therein. Such an apparatus preferably further comprises bracket means for supporting the receptacle means relative to a microtome, with the interior channel situated at a predetermined angle relative the microtome blade means for optimized passage of specimen slices into the interior channel.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which.

Repeat use of reference characters throughout the present specification and appended drawings is intended to represent same or analogous features or elements of the invention.

DETAILED DESCRIPTION OF THE PREFERRED EMBODIMENTS

Figure 1:
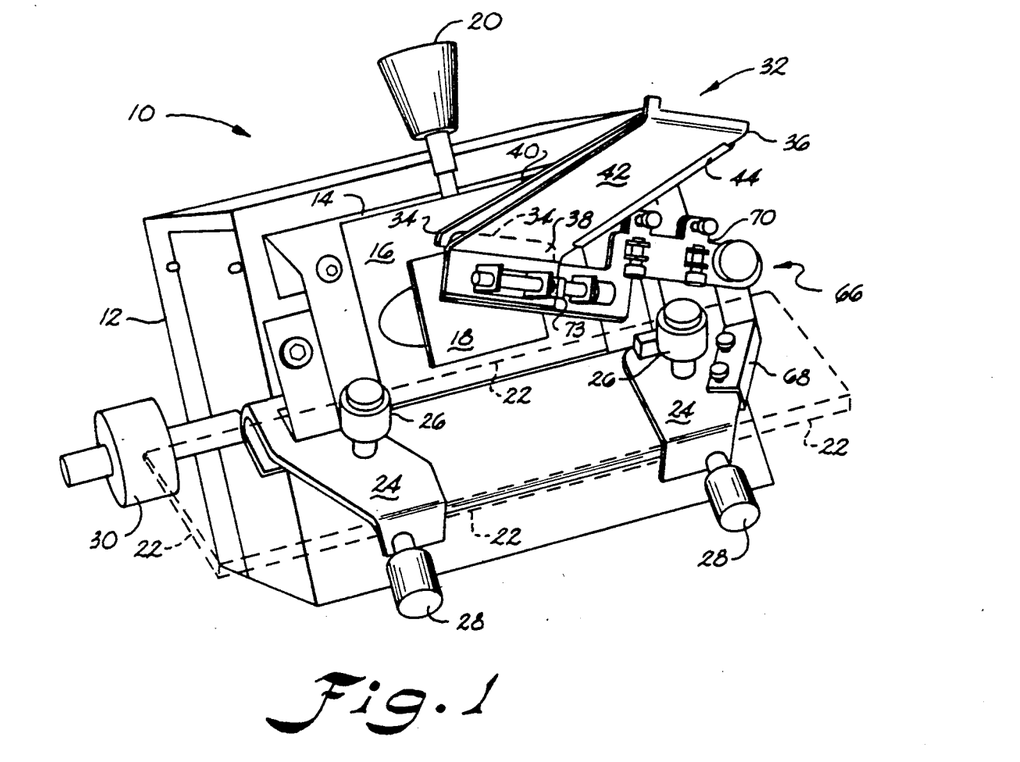
FIG. 1 is a plan view of an exemplary embodiment of the present invention illustrating use thereof with an exemplary conventional microtome.

With reference to the figures, exemplary preferred embodiments of the present invention are described in detail. One preferred embodiment of a present apparatus for receiving specimen slices is shown in FIG. 1. FIG. 1 also represents a typical conventional microtome 10 which includes a microtome frame 12 with a chuck 14 adapted to secure a tissue sample block 16 to the microtome frame. Tissue sample block 16 is adapted to have secured thereto by conventional means a tissue sample 18. A chuck knob 20 controls the action of chuck 14, as understood by those of ordinary skill in the art.

The microtome further includes, supported in frame 12, a means for cutting a tissue sample. As representatively embodied herein, this cutting or blade means includes a blade 22 (shown in dotted-line for clarity of illustration) fixedly secured to frame 12 with a blade holder 24 and a pair of holding screws 26. The blade holder also includes a pair of elevating screws 28 for selective adjustment of the blade. The conventional microtome still further includes means for advancing the tissue sample into contact with the blade to produce specimen slices. Such advancing means are of a conventional type and may be controlled by an increment adjusting knob 30, as illustrated in FIG. 1, operation and function of which is well known to those of ordinary skill in the art without further explanation. As known, blade 22 is usually fixed, and tissue specimen 18 is moved relative thereto for being cut into thin slices (later illustrated and discussed).

As illustrated in FIG. 1, an apparatus for receiving specimen slices in accordance with the present invention includes an improved shield mechanism or receptacle means 32 adapted for receiving specimen slices. As representatively illustrated in FIGS. 1 and 2, slice receiver 32 includes a first end 34 for being located proximate the microtome cutting means and the tissue sample, and a second end 36 for being located opposite the first end (i.e., distal to the tissue specimen 18). As illustrated in FIGS. 1 and 3, the slice receptacle means (i.e., tissue slice receipt channel means) 32 is adapted to receive specimen or tissue slices through an opening 38 at first end 34. To facilitate reception of multiple, successive slices, the specimen slice receptacle means is preferably rectangular and elongated in a direction away from the microtome. Receptacles shorter than those presently illustrated may be used for receiving fewer tissue slices than the number thereof shown.

Figure 4A:
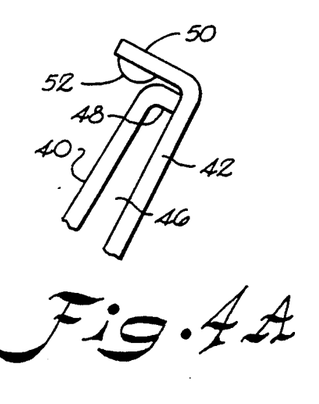
FIG. 4A is an enlarged side view of a distal end portion of the exemplary embodiment shown in FIGS. 2 through 4.
Figure 5:
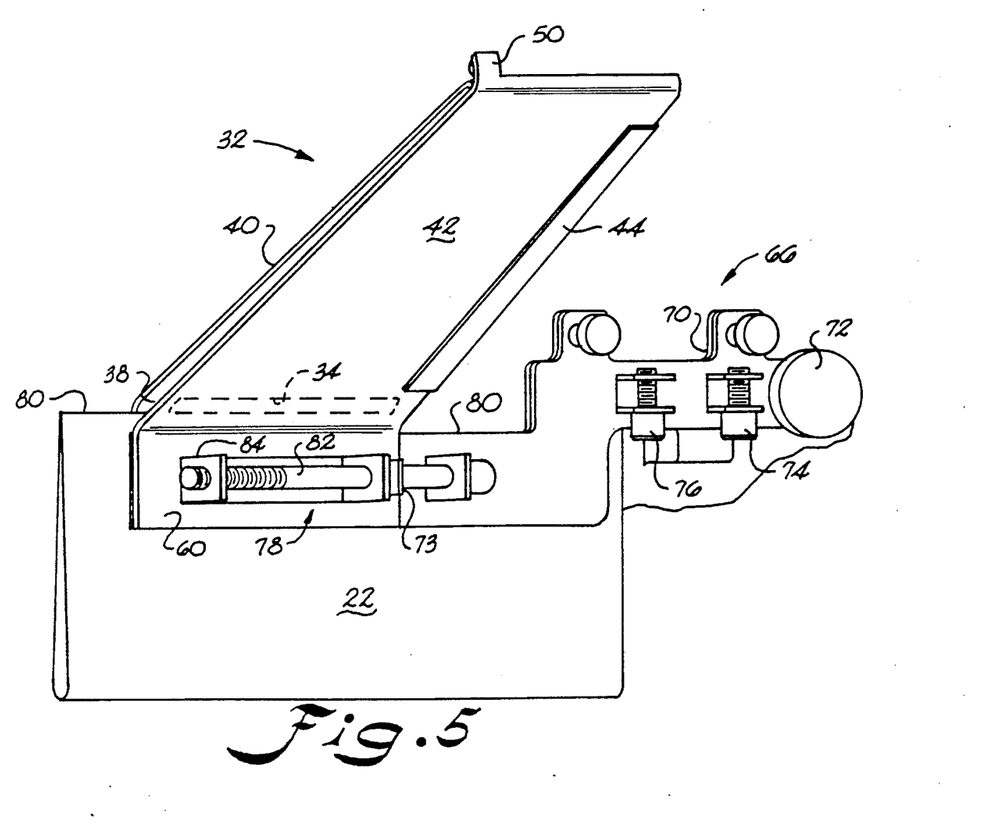
FIG. 5 is a plan view of exemplary present adjustable support features, in combination with exemplary present tissue slice receiving features, all in accordance with the present invention.
Figure 6:
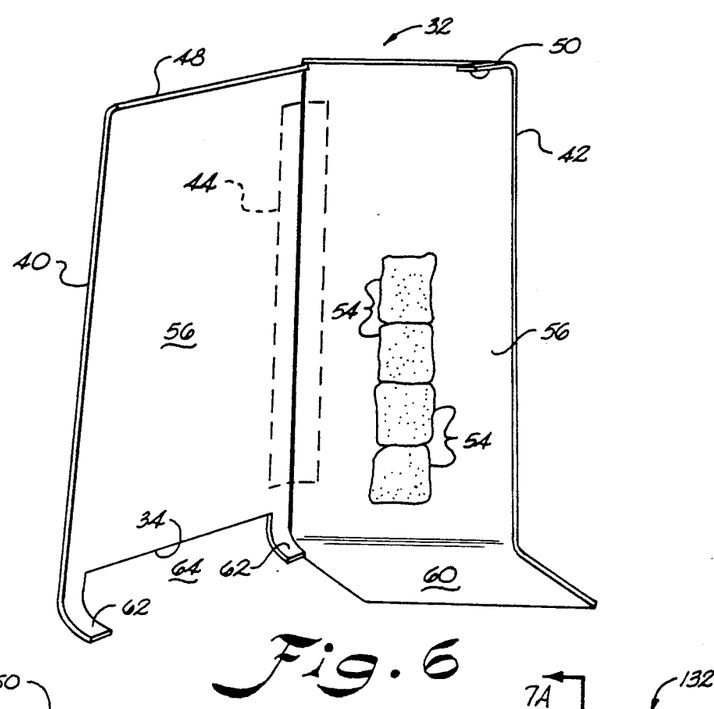
FIG. 6 is a plan view of a present exemplary tissue slice receiver embodiment, in an opened position thereof.
Figure 7:
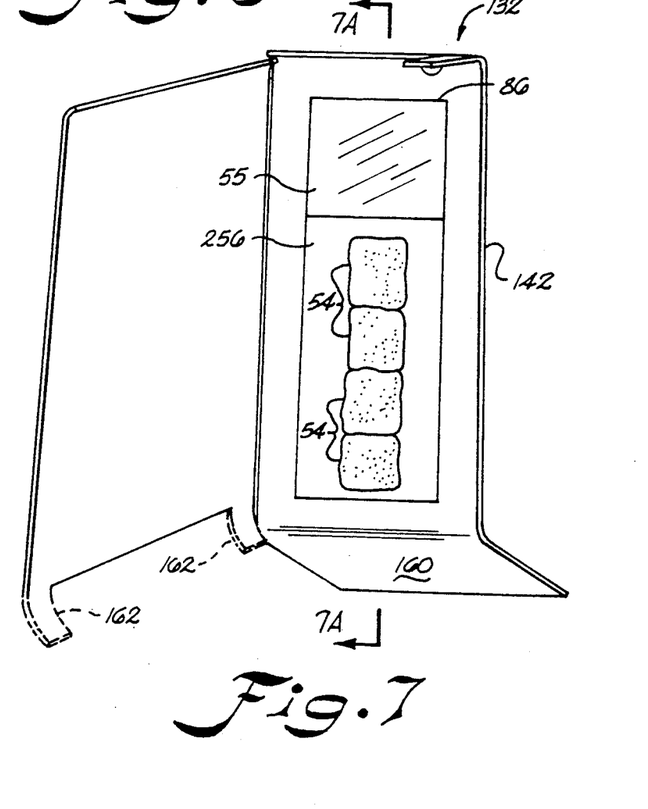
FIG. 7 illustrates a plan view of an exemplary alternate tissue slice receiver embodiment (in an opened position) of the present invention.

As illustrated in FIGS. 1 and 6, the slice receiving device 32 includes an upper (first) member 40 pivotably attached to a lower (second) member 42 by a hinge 44. The slice receiving device is adapted for members 40 and 42 to selectively be relatively pivoted between an opened position (such as illustrated in FIGS. 6 and 7) and a closed position (such as in FIGS. 1 and 5). As variously illustrated (such as in FIG. 2), upper and lower members 40 and 42 define a space 46 (or interior channel or chamber) therebetween whenever situated in their closed position for receipt of specimen slices. As best illustrated in FIG. 4A, upper member 40 includes a spacing portion 48 which extends at an angle from upper member 40 in the direction of (and engages with) lower member 42 when the device 32 is in a closed position, to help define the space between the upper and lower members. All or a portion of member 42 may be transparent for improved slice visualization, as represented by the dotted-line portion of end 34 in present FIGS. 1 and 5.

In one preferred embodiment, lower member 42 may include a locking extension portion 50 which extends in the direction of the upper member when the receiver is in its closed position. The locking extension portion includes a locking protrusion 52 which is adapted to engage upper member 40 whenever it is in the closed position for securing the first and second members 40 and 42 in their closed position. As should be apparent, a slight amount of structural flexing (not shown) may accommodate such engagement action (and a corresponding disengagement action). Whenever the receiver is closed, the slices are stored, protected, and portable; whenever the receiver is opened, the slices are accessible and removable.

Figure 2:
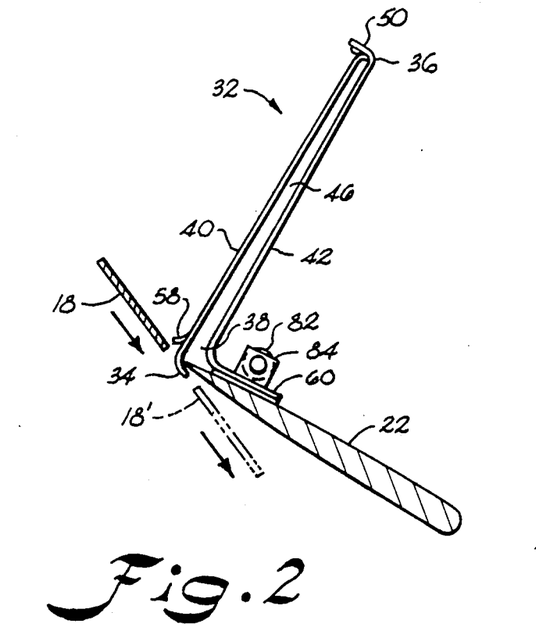
FIG. 2 is an enlarged side view of the exemplary embodiment represented in FIG. 1, prior to receiving tissue slices.
Figure 3:
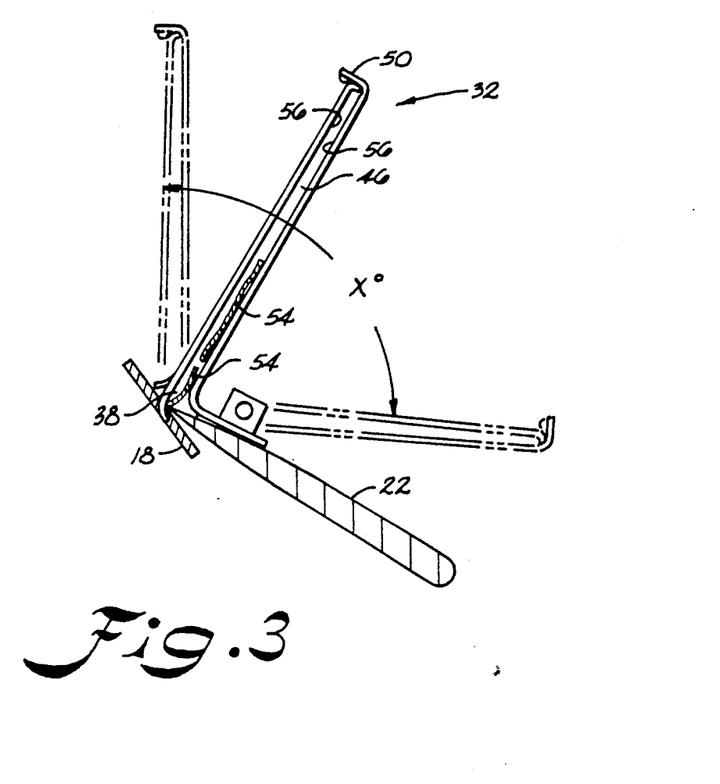
FIG. 3 is another enlarged side view of the exemplary embodiment of FIG. 1, as it is receiving tissue slices.
Figure 3A:
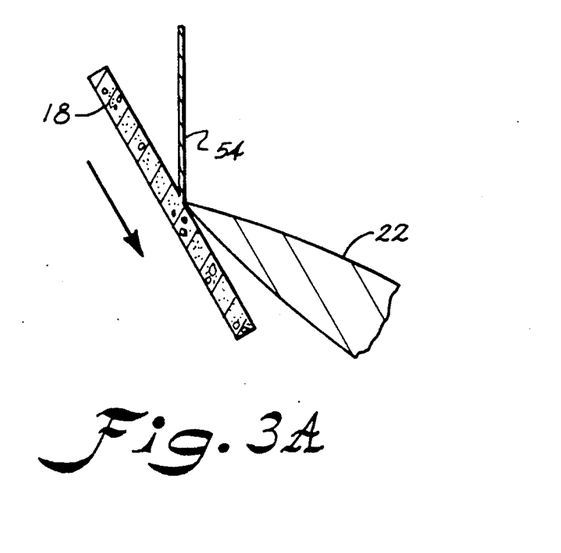
FIG. 3A is a further enlarged side cross-sectional view of a specimen slice being cut from a tissue sample by a microtome blade.

FIG. 3A illustrates a tissue sample 18 being cut by blade 22 to produce a relatively thin, planar specimen slice 54. The specimen 18 is intended as representative of a cryogenic conditioned specimen, which may be frozen at some relatively low temperature, such as about ($-20°$) Celsius. As illustrated by FIG. 3A, the natural direction of the slice when being cut from the cryogenic sample by the blade is away from the blade, as oriented in that Figure, rather than downward along the top of the blade. The solid arrows beneath specimen 18 in FIGS. 2 and 3A represent relative movement between such specimen and the blade means, whereby thin slices 54 are produced.

As illustrated in FIGS. 2 and 3, the slice receiving device 32 in accordance with this invention is adapted to be attached to or supported relative the microtome such that the tissue slice receipt channel 46 between the upper and lower members of the invention is oriented substantially in the same general direction that the specimen slices naturally take when being cut by the blade.

The solid line representation of FIG. 3 shows an approximately 90° angle between receipt channel 46 and blade 22. In accordance with this invention, such angle is preferably predetermined with the support features of this invention, and preferably falls generally within a range of from about 25° to about 90°. Exact cutting conditions can dictate various selections within such range. However, placements of channel 46 within a broader angle range "X°", such as represented in dotted line illustration by FIG. 3 (covering a range of approximately 25° to 120° relative blade 22) may be practiced in accordance with the present invention.

Figure 4:
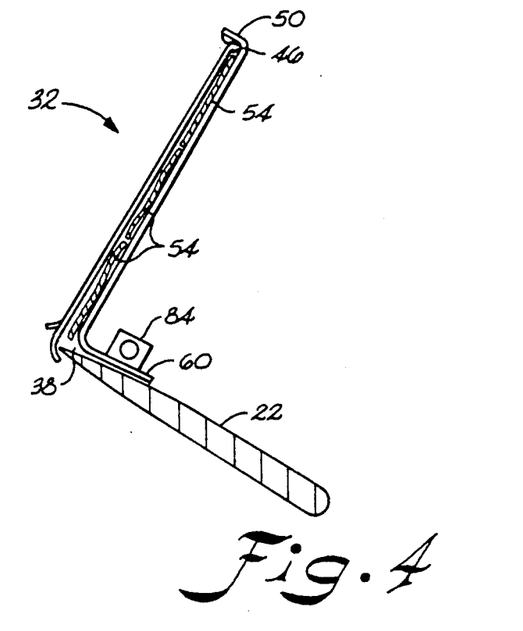
FIG. 4 is still another enlarged side view of the exemplary embodiment of FIG. 1, after receiving a full complement of tissue slices.

As best illustrated in FIGS. 3 and 4, as the sample 18 is cut with blade 22, the specimen slices 54 proceed into the specimen slice receipt channel 46 in a ribbon-like or sequential fashion. Channel 46 is relatively enlarged in the drawings for clarity in its illustration. In actuality, such channel is preferably "paper thin", just as the slices themselves. Such paper thin or "micro" space can be accomplished in a variety of ways, such as by having border regions of members 40 and 42 slightly thicker than their central portions so that the two plates would be slightly apart in such central channel region. The inner surfaces 56 (see FIG. 3) of upper and lower members of the specimen slice receipt channel 46 guide each slice by engagement therewith, so as to prevent the specimen slices 54 from rolling or curling after they are cut. Each subsequent slice forces the previous slice further into channel 46 (see FIG. 3) until the channel is full (see FIG. 4). Preferably, inner surfaces 56 have coatings comprising non-stick materials, such as Teflon, or the like.

As best illustrated in FIG. 2, upper member 40 of the slice receiver means or shield mechanism 32 has a guide lip 58 relatively adjacent its first end 34 for guiding each specimen slice into the specimen slice receipt channel 46. Dotted line representation 18' of FIG. 2 generally represents relative movement of the tissue sample past blade means 22. It will be apparent from this disclosure to one skilled in the art that the angle of the specimen slice receipt channel with respect to the blade 22 and tissue sample 18 may be selected to provide the most suitable natural path of the specimen slice 54 into the interior chamber 46, such as discussed above with reference to FIG. 3.

As illustrated in FIG. 6, receptacle means 32 is adapted to be opened by pivoting upper member 40 away from lower member 42 about hinge means 44. Various types and constructions of hinge means may be practiced. When the specimen slice receiving device 32 is in its opened position, there is ready access to the specimen slices 54 received in the interior chamber 46 thereof to permit transfer of slices 54 to a slide or equivalent for microscopic or other evaluation.

As further illustrated in FIG. 6, lower member 42 of the specimen slice receptacle means 32 includes a lower member support section 60, which is adapted to rest on blade means 22 (as illustrated in FIGS. 2 and 5) whenever receptacle means 32 is positioned for receiving specimen slices (i.e., properly situated with its interior channel opening 38 relatively adjacent blade means 22). Upper member 40 of receptacle means 32 may include a pair of upper member support sections 62, as best illustrated in FIG. 6. Upper member support sections 62 collectively with first end 34 of upper member 40 form a U-shape, whereby the specimen slices may enter interior channel 46, passing through both opening 38 and the space 64 formed between the two members 62. Members 62 are curved in a direction opposite guide lip 58, and may be adapted to extend slightly around the tip of the blade, whereby in combination with lower member support section 60 the specimen slice receiver device is securely positioned with respect to blade 22. Alternatively, other measures may be taken for proper and adequate securement of the device, wherefore members 62 may be omitted (as represented by the dotted-line illustration of members 162 in present FIG. 7).

As illustrated in FIGS. 1 and 5, an embodiment of the present specimen slice receiving apparatus or shield mechanism may further include support or bracket means 66 for supporting receptacle means 32 relative to a microtome. Such support means 66 may assume numerous shapes, sizes and constructions, but preferably attaches receptacle means 32 to the microtome. More preferably, means 66 pivotably and removably so attaches means 32. Further, means 32 are adjustably mounted by means 66, with such adjustability being actuable in respective plural, independent axes, such as in part represented by FIG. 3.

As embodied herein, and as illustrated in FIG. 1 as one exemplary preferred embodiment, means 66 includes a bracket attachment member 68 adapted to attach directly to the microtome, and an adjustable receptacle means bracket 70 adapted to adjustably connect receptacle means 32 with bracket attachment member 68. As embodied herein and illustrated in FIG. 5, adjustable receiver means bracket 70 includes a horizontal pivot axis mechanism 72 whereby the entire receptacle means 32 can be selectively pivoted away from blade 22 and tissue sample 18, so that rough and unwanted specimen slices can be cut without their entering the specimen slice receptacle channel 46. This is desirable so that the rough tissue sample can be shaved down to an appropriate level so that only suitable specimen slices enter interior channel 46 after means 32 is pivoted back into proper position (such as in FIGS. 1 and 5). Alternative pivoting mechanisms may be practiced. For example, a hinge mechanism 73 may be provided for upward pivoting of receptacle means 32 from blade means 22. Such arrangement is particularly useful with embodiments of the present invention which do not make use of support members 62 (see the reference to FIG. 7, supra).

The adjustable receiver means bracket 70 also includes vertical adjustment and positioning screw mechanisms 74 and 76 for adjusting the relative vertical position and attitude of the specimen slice receptacle means 32. The adjustable receiver means bracket 70 further includes a lateral adjustment mechanism 78 for adjusting the position of the specimen slice receptacle means 32 (and its tissue slice receipt channel 46) laterally relative the edge 80 of blade 22. Mechanism 78 (like all present adjustment mechanisms) may assume various forms, but preferably as illustrated includes a threaded member 82 for threadable engagement with at least one member 84, which is fixedly received relative support area 60. It is generally intended that any attachment mechanism 66 which provides for the desired locating of receptacle means opening 38 relative blade edge 80 and with the desired attitude (i.e., angle) of interior channel 46 thereto, falls within the spirit and scope of the present invention.

Figure 7A:
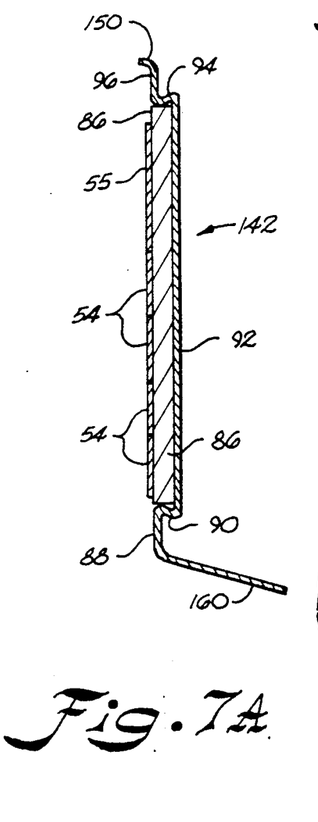
FIG. 7A is a side cross-sectional view of the alternate embodiment of FIG. 7, take along the line 7A—7A indicated on such figure.

FIGS. 7 and 7A illustrate an alternate preferred embodiment of specimen slice receptacle means 32 in accordance with the present invention. FIG. 7 is a plan, opened position illustration generally similar in view perspective to that of FIG. 6. FIG. 7A is a generally side cross-sectional view taken along the line 7A—7A indicated in FIG. 7. In such embodiment, lower member 142 of specimen slice receptacle means 132 includes means adapted for receiving a slide 86. As embodied herein, and as illustrated more particularly in FIG. 7A, such slide receiving means include a first generally vertical portion 88 extending from support section 160 and connected to a first generally horizontal portion 90, which in turn is connected to a second generally vertical portion 92 which extends approximately the length of a conventional microscope slide 86. The second vertical portion 92 is connected to a second horizontal portion 94, which in turn is connected to a third vertical portion 96. The horizontal portions 90 and 94 are the approximate length of the thickness of a conventional microscope slide, whereby a slide 86 may be placed in the indented or recessed portion of the lower member 142 of this embodiment.

With the embodiment of FIGS. 7 and 7A, whenever receptacle means 132 is in its closed position and properly situated as a tissue sample is sliced, the specimen slices 54 proceed into the space between members 140 and 142 as in the earlier embodiments. In such instance, slide 86 acts as a receiving or inner surface for lower member 142. After the desired number of slices are deposited on slide 86, upper member 140 can be pivoted into an opened position and slide 86 removed with specimen slices thereon, thus eliminating the necessity of transferring the specimen slices 54 from the inner surface 56 of member 42 to a slide. Area 55 of slide 86 may be frosted for labeling.

Figure 8:
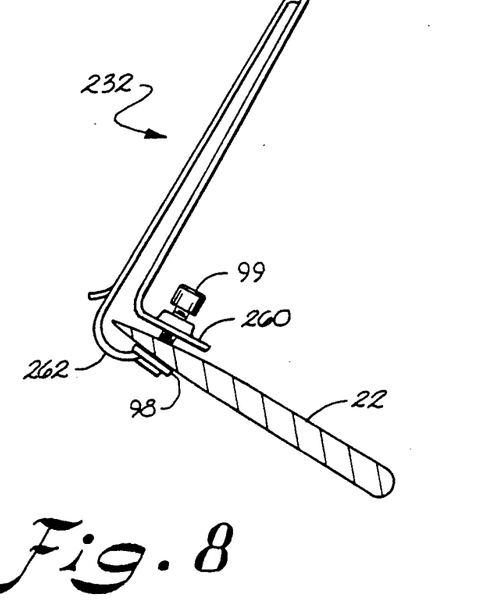
FIG. 8 is a side view of a still further alternate tissue slice receiver embodiment of the present invention, also illustrating further alternate present fastening features.

FIG. 8 illustrates yet another alternate exemplary preferred embodiment of specimen slice receptacle means 232 per this invention. As embodied therein, upper member support section 262 includes a support pad 98 for engagement with blade 22, and lower member support section 260 defines a threaded hole therein (not seen) and includes a clamping screw 99, whereby specimen slice receptacle means 232 can be clamped to blade 22 for enhanced rigidity during the slicing operation.

Figure 9:
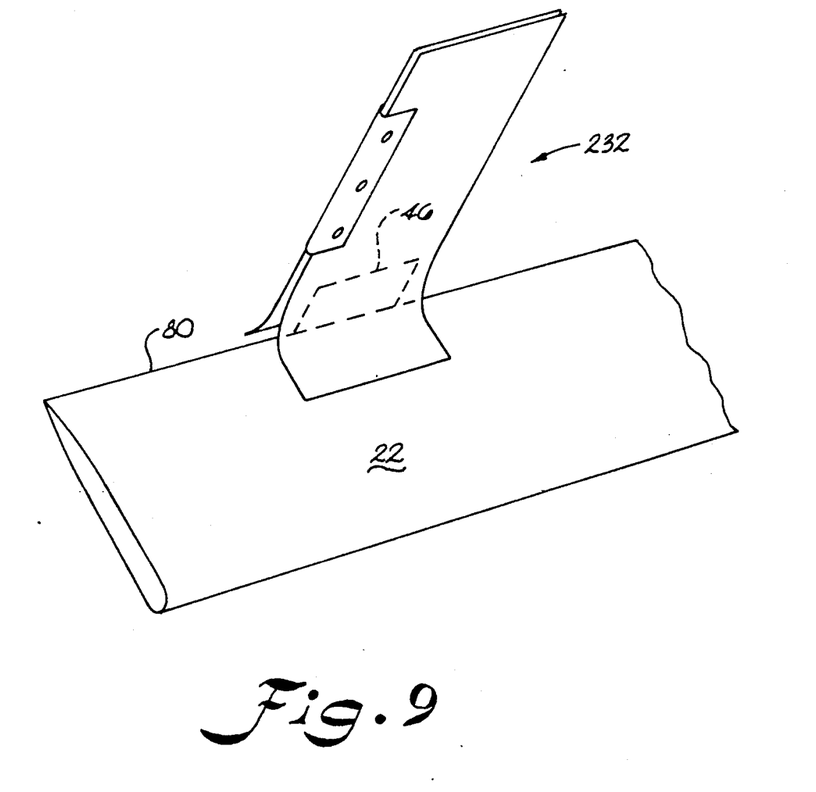
FIG. 9 is a plan view showing exemplary present slice receptacle means, positioned relative blade means, with all of the foregoing in isolation from other present features, for clarity in illustration thereof.

FIG. 9 is a plan view illustrating only a desired exemplary relationship between representative receptacle means 232 in accordance with this invention and blade means 22. The view of FIG. 9 supplements that of, for example, present FIGS. 2 and 8, which do not directly illustrate the full operative relationship of present structures relative blade means. FIG. 9, on the other hand, does illustrate the unobstructed passage of tissue slices which is provided from edge 80 of blade means 22 into channel 46, without interference from members 262 (when used).

It is generally preferred for all embodiments that the upper and lower members be constructed of a material which allows the specimen slices to easily slide in the generally thin, planar interior space therebetween. It will also be apparent to one skilled in the art that the interior of the receiver may be coated with Teflon or an equivalent to facilitate such sliding of the slices. Obviously, an embodiment such as that of FIG. 7 does not require special coatings on the inner surface of member 142 residing beneath slide 86 since the surface of the slide itself rather than member 142 is in contact with the tissue slices.

Various additional practices are not precluded from combination with the present invention. For example, the upper and lower members may be made of different materials so that static electricity will hold the tissue slices against one side, further assisting with keeping the specimen slices flat. Also, a charge of static electricity could be introduced to the receptacle means to assure flatness of specimen slices and to cause the slices to adhere to only one inner surface of the interior channel. It will be apparent to one skilled in the art that such a static electricity charge could be generated in any conventional manner, and further that the specimen slices could be given a charge opposite the charge on such one member of the specimen slice receiver so as to likewise enhance the adhesion of the specimen slices to one interior surface of the specimen slice receiver.

Likewise, various materials may be used in practicing the present invention. For instance, it will be apparent to those skilled in the art that the specimen receptacle means hinge 44 can be constructed of any suitable material such as, for example, mylar, and that selected portions or all of members 40 and 42 may be transparent to allow monitoring of tissue slices as they proceed in the planar interior channel 46.

It will be understood, of course, that while the form of the invention herein shown and described constitutes preferred embodiments of the invention, it is not intended to illustrate all possible forms of the invention. It will also be understood that the words used are words of description rather than of limitation, and that various changes may be made without departing from the spirit and scope of the broader invention herein disclosed and set forth in the appended claims.

What is claimed is:

1. An improved shield mechanism for use with a microtome having a blade for cutting tissue slices from a tissue specimen, said shield mechanism comprising:
   first and second members cooperatively arranged so as to define a tissue slice receipt channel therebetween and an opening to said channel; and
   support means for supporting said first and second members relative the microtome such that said opening is situated relatively adjacent the microtome blade;
   whereby tissue slices cut from a tissue specimen with the microtome enter said tissue slice receipt channel through said opening, for storage of such tissue slices within said receipt channel; and
   wherein said support means adjustably supports said members relative the microtome, with such adjustability being selectively actuable in separate, plural axes.

2. An improved shield mechanism as in claim 1, wherein said first and second members comprise generally planar members pivotably supported relative one another, so that tissue slices received therebetween may be subsequently accessed by pivoting said members into a relatively opened position.

3. An improved shield mechanism as in claim 1, wherein at least one of said members includes a curved lip adjacent said receipt channel opening for guiding tissue slices into said receipt channel.

4. An improved shield mechanism as in claim 1, wherein said tissue slice receipt channel is relatively thin and planar for flat storage of tissue slices therein, without curling of such tissue slices, due to guiding contact of such tissue slices with the inner surfaces of said receipt channel.

5. An improved shield mechanism as in claim 4, wherein said receipt channel inner surfaces have coatings comprising nonstick materials.

6. An improved shield mechanism as in claim 1, wherein said first and second members are removably supported by said support means, to facilitate separation and transport of stored tissue slices from the microtome which produced such slices.

7. An improved shield mechanism as in claim 1, wherein said first and second members are mutually pivotably supported as a unit by said support means relative the microtome, whereby said receipt channel and said opening thereof may be temporarily selectively displaced from relatively adjacent the microtome blade, to prevent entry into said receipt channel of unsuitable tissue samples such as those initially cut from a tissue specimen, and whereby said receipt channel and opening may be subsequently selectively pivoted back for receipt of suitable tissue slices.

8. An improved shield mechanism as in claim 1, wherein said support means adjustably supports said tissue slice receipt channel within a range of predetermined angles relative the microtome blade, for optimized receipt of tissue slices therein without curling of such slices.

9. An improved shield mechanism as in claim 8, wherein said predetermined angles are preferably in a range generally from about 25° to about 90°.

10. An improved shield mechanism as in claim 1, wherein at least one of said members is at least partially transparent to permit visual monitoring of tissue slices within said tissue slice receipt channel.

11. An improved shield mechanism as in claim 1, wherein one of said members includes a spacing portion extending in the direction of the other of said members for engaging such other member and for establishing a substantially planar space between said members so as to define said tissue slice receipt channel.

12. An improved shield mechanism for use with a microtome having a blade for cutting tissue slices from a tissue specimen, said shield mechanism comprising:
   first and second members cooperatively arranged so as to define tissue slice receipt channel means therebetween for receiving tissue slices and an opening to said channel means; and
   support means for supporting said first and second members relative the microtome such that said opening is situated relatively adjacent the microtome blade;
   so that tissue slices cut from a tissue specimen with the microtome enter said tissue slice receipt channel means through said opening, for storage of such tissue slices within said receipt channel means;
   wherein said first and second members comprise generally planar members pivotably supported relative one another, so that tissue slices received therebetween may be subsequently accessed by pivoting said members into a relatively opened position; and
   said mechanism further including a planar slide, removably supported within said tissue slice receipt channel means for supporting tissue slices thereon, so that said slide with tissue slices thereon is immediately available for examination upon pivoting of said members into said relatively opened position thereof.

13. An improved shield mechanism for use with a microtome having a blade for cutting tissue slices from a tissue specimen, said shield mechanism comprising:
   first and second members cooperatively arranged so as to define tissue slice receipt channel means therebetween for receiving tissue slices and an opening to said channel means; and p1 support means for supporting said first and second members relative the microtome such that said opening is situated relatively adjacent the microtome blade;
   so that tissue slices cut from a tissue specimen with the microtome enter said tissue slice receipt channel means through said opening, for storage of such tissue slices within said receipt channel means;
   wherein said tissue slice receipt channel means is relatively thin and planar for flat storage of tissue slices therein, without curling of such tissue slices, due to guiding contact of such tissue slices with the inner surfaces of said receipt channel means; and wherein said receipt channel means inner surfaces have coatings comprising nonstick materials.

14. An improved shield mechanism for use with a microtome having a blade for cutting tissue slices from a tissue specimen, said shield mechanism comprising:

first and second members cooperatively arranged so as to define tissue slice receipt channel means therebetween for receiving tissue slices and an opening to said channel means; and support means for supporting said first and second members relative the microtome such that said opening is situated relatively adjacent the microtome blade;

so that tissue slices cut from a tissue specimen with the microtome enter said tissue slice receipt channel means through said opening, for storage of such tissue slices within said receipt channel means;

wherein at least one of said members is at least partially transparent to permit visual monitoring of tissue slices within said tissue slice receipt channel means.

15. A specimen slice receiving apparatus adapted for receiving specimen slices from a cryogenic microtome of the type including cutting means for cutting a tissue sample to produce specimen slices, said specimen slice receiving apparatus including receptacle means for receiving specimen slices, said receptacle means including a first end thereof for being located proximate the microtome cutting means, a second end located opposite said first end, an interior chamber for receiving specimen slices, and an opening defined proximate said first end and in communication with said interior chamber, wherein said receptacle means is adapted for receiving specimen slices into said interior chamber thereof, passing through said opening at said first end thereof; and further including means for pivotably attaching said receptacle means to a microtome, whereby said receptacle means may be selectively positioned adjacent the microtome cutting means for receiving specimen slices therefrom.

16. A specimen slice receiving apparatus as defined in claim 15, wherein said receptacle means includes an upper member pivotably attached to a lower member and adapted to be pivoted between respective opened and closed positions, said upper and lower members defining a space therebetween comprising said interior chamber whenever said upper member is in said closed position thereof.

17. A specimen slice receiving apparatus as defined in claim 16, wherein said upper member of said receptacle means includes a flared lip at said first end thereof, for guiding specimen slices into said space as they are cut from a tissue sample by the microtome.

18. A specimen slice receiving apparatus as defined in claim 16, wherein said upper member includes a spacing portion extending in the direction of said lower member for engaging said lower member wherever said upper member is pivoted to said closed position thereof, for establishing said space between said members.

19. A specimen slice receiving apparatus as defined in claim 16, wherein said lower member includes means for receiving a slide within said receptacle means interior chamber, whereby specimen slices may be received directly on a slide within said interior chamber.

20. A specimen slice receiving apparatus as defined in claim 15, wherein said interior chamber is relatively thin and generally planar, and said receptacle means is oriented so that said interior chamber is aligned with the natural direction taken by specimen slices as they are cut from a tissue sample by the microtome cutting means, whereby such slices proceed up said planar interior chamber in a flat state without any curling.

21. An apparatus for receiving specimen slices from a cryogenic microtome having blade means for cutting a tissue sample to produce specimen slices, said specimen slice receiving apparatus comprising:

generally planar receptacle means for receiving specimen slices, said receptacle means including a first end for being located proximate the microtome blade means and having an opening thereinto, a second end for being located distal of the microtome blade means, and a generally planar interior channel, whereby said receptacle means may receive specimen slices in a flat condition at said first end thereof and store same within said interior channel thereof;

said receptacle means including an upper member pivotably attached to a lower member and adapted to be pivoted between respective opened and closed positions, said upper and lower members defining a substantially planar space therebetween comprising said interior channel when situated in said closed position so as to receive specimen slices therein; and said apparatus further comprising bracket means for supporting said receptacle means relative to a microtome, with said interior channel situated at a predetermined angle relative the microtome blade means for optimized passage of specimen slices into said interior channel.

22. Apparatus as in claim 21, wherein said predetermined angle is preferably in a range generally from about 25° to about 90°, and wherein said bracket means adjustably, pivotably, and removably supports said receptacle means on the microtome, with such adjustability being in respective, plural axes.

23. Apparatus as in claim 21, further including slide means removably supported within said receptacle means interior channel, for receiving specimen slices directly thereon, whereby said slide means with specimen slices thereon may be removed from said receptacle means wherever it is in its opened position.

24. Apparatus as in claim 21, wherein said receptacle means is at least partially transparent to permit visual observation of specimen slices received therein.

25. Apparatus as in claim 21 wherein at least one of said upper and lower members includes a curved lip adjacent said first end opening for guiding specimen slices into said interior channel.

26. Apparatus as in claim 21, wherein inner surfaces of said interior channel have coatings comprising nonstick materials.

27. Apparatus as in claim 21, wherein said upper member includes a spacing portion extending in the direction of said lower member for engaging said lower member whenever said upper member is pivoted to said closed position thereof, for establishing said substantially planar space between said members.

28. A specimen slice receiving apparatus adapted for receiving specimen slices from a cryogenic microtome of the type including cutting means for cutting a tissue sample to produce specimen slices, said specimen slice receiving apparatus including receptacle means for receiving specimen slices, said receptacle means including a first end thereof for being located proximate the microtome cutting means, a second end located opposite said first end, an interior chamber for receiving specimen slices, and an opening defined proximate said first end and in communication with said interior chamber, wherein said receptacle means is adapted for receiving specimen slices into said interior chamber thereof, passing through said opening at said first end thereof; further including bracket means, mounted on a microtome, for supporting said receptacle means relative such microtome for use therewith; wherein said receptacle means is removably and pivotably supported by said bracket means, and said support with said bracket means is selectively and independently adjustable in plural axes.

* * * * *